United States Patent [19]

Flynn

[11] Patent Number: 4,532,923
[45] Date of Patent: Aug. 6, 1985

[54] AIR BAG

[75] Inventor: Stephen D. Flynn, Oakville, Canada

[73] Assignee: D-Two Systems International Inc., Mississauga, Canada

[21] Appl. No.: 519,754

[22] Filed: Aug. 2, 1983

[51] Int. Cl.³ ............................................. A61M 16/00
[52] U.S. Cl. .................................. 128/205.13; 92/92; 604/185
[58] Field of Search ....................... 128/205.13, 205.16, 128/205.17, 203.28, 202.22; 604/37, 75, 185, 212, 213, 216; 92/92

[56] References Cited

U.S. PATENT DOCUMENTS

| | | | |
|---|---|---|---|
| 3,009,459 | 11/1961 | Ruben | 92/92 |
| 3,262,446 | 7/1966 | Stoner | 128/205.13 |
| 3,363,833 | 1/1968 | Laerdal | 128/205.13 |
| 3,473,529 | 10/1969 | Wallace | 128/205.13 |
| 4,077,404 | 3/1978 | Elam | 128/205.13 |
| 4,405,321 | 9/1983 | Budoff | 604/212 |

FOREIGN PATENT DOCUMENTS 74811  1/1961  France ............................ 128/205.13

*Primary Examiner*—Henry J. Recla
*Attorney, Agent, or Firm*—George A. Rolston

[57] ABSTRACT

A manually operable resuscitator bag of one-piece construction having a generally elongated football shape, an inlet at one said end, and an outlet at the other end, fold-rings in each end portion having walls of reduced thickness, whereby the ends may be telescoped, ridges of thickened wall section between the fold-rings, the center of the bag having a wall thickness equal to the thickness of said ridges in the tapering ends between the fold-rings, and longitudinal ribs formed on the outer surface of the center of the bag spaced around the circumference, providing increased resiliency and a rapid recovery for the shape of the bag.

1 Claim, 3 Drawing Figures

AIR BAG

The invention relates to a resuscitator device, for the treatment of persons suffering from breathing difficulties, and in particular, to a manually operable pressure bag, by means of which air or gas is supplied to such a person.

BACKGROUND OF THE INVENTION

Resuscitation of persons suffering from breathing difficulties is required in a great many different circumstances. It may be required for example, in a hospital or medical operating room. It is frequently required in emergency vehicles such as ambulances, fire appliances, rescue vehicles, life boats and the like. Resuscitation is frequently required in sporting locations, particularly, where water sports are carried on, and in many working environments such as mines, on hydro electrical service vehicles, and in many different military vehicles and installation, which are too numerous to mention.

It is well known that resuscitation may be carried out initially on an emergency basis by mouth to mouth methods. However, it is much more satisfactory to supply fresh air rather than rebreathed air, and better still, to supply air enriched with gas or in certain circumstances, special gas breathing mixtures. In addition, the effort required for mouth to mouth resuscitation is very great, and it can leave an assistant exhausted after only a few minutes.

Consequently, for all these reasons, it is highly desirable to provide some form of simple, manually operated resuscitation equipment, by means of which fresh air, or if available, some form of gas/air or gas mixture, can be supplied to a person suffering from breathing difficulties in an emergency. For reasons of economy, it is necessary that such equipment should be as simple as possible, and preferably manually operated so that it does not require to be connected to a power source.

For this purpose, numerous forms of apparatus have been proposed which are based essentially on a flexible bag or bellows-like device, which may function as an air pump, so that it may be manually squeezed to force air into the lungs of a patient.

Such air bags must however, be capable of being stored in a small space or compartment or in a small emergency pack. They must have a very extended shelf life without any requirement for inspection or testing or servicing, and they must be instantly ready for use as soon as the pack is open. They must operate in a reliable, efficient manner in this way in an emergency which may not occur for years after the equipment has been put in place. Such equipment may be subjected to extremes of weather and temperature, and must be resistent so that it will function even in extremes of heat and cold.

It must also be resistant to moisture which might cause rust in a metal structure, and be resistant to other forms of decay.

One form of air bag has been proposed, in U.S. Pat. No. 3,363,833 which is formed of an integral one piece construction, being molded from a thermoplastic material. The bag described in such patent is of such a type that it can be collapsed for packing, and storage, and is yet ready for use when unpacked. The bag is designed in such a way as to incorporate a wall area around the center of the bag which is of thin-wall construction, so that the user can more readily sense the pressure in the bag. Apparently, it was felt at the time that that product was being developed, that the ability to feel the pressure within the bag was essential to the safe usage of the bag. The theory was that where a person was not in fact breathing at all, or was breathing only with great difficulty, and where the bag was being used to force air into the lungs so as to actually dilate them, that a user of the bag might inadvertently apply excessive pressure to the bag thereby causing damage to the lungs.

There is no doubt that over pressure applied to the lungs especially in the case of small children, can cause damage.

In practice however, it has been found by experience that a bag designed in this way had certain disadvantages which caused even greater problems.

In situations particularly where breathing is arrested or is taking place only with great difficulty, resuscitation is being carried out in haste, and often with feelings of considerable anxiety or even fear, on the part of the assistant or person applying the treatment.

It is well known that unless breathing is restarted within a very short period of time, that irreversible brain damage will take place leading rapidly to death.

Accordingly, the assistant will usually be highly agitated when using the bag, and will be anxiously watching for signs of breathing restarting.

One of the disadvantageous features of the bag described in the above-mentioned patent is that due to its thin-wall construction, it tended to collapse too easily. Once collapsed, the bag then took a considerable length of time to recover to its normal shape. There are no internal springs in such bag for the reasons given above, and it must rely on its own inherent resiliency to recover its original shape. Until it has recovered its own original shape, it is not possible for the operator to compress it again to create a further positive pressure for the patient. During normal non-emergency breathing assistance, the bag will not be compressed more than once for each breath of the patient. Since the normal patient will not inhale more frequently than about thirty to forty inhalations per minute, and provided the recovery time for the bag is no longer than about ½ second in length, then there is no problem. However, during emergency resuscitation, when a person is not breathing, the best medical practice recommends that four or five short, sharp pulses of positive pressure should be applied rapidly in quick succession. These initial pulses may be in the order of two or three per second. The slow recovery rate of the bag described in such patent therefore rendered it difficult if not impossible to apply these initial rapid pressure pulses.

In addition to this disadvantage, the slow recovery rate of the bag was, to many operators, an additional cause of stress and worry. The operator, in each cycle, must compress the bag gradually, with a graduated carefully controlled manual pressure and must then release it, waiting for the bag to recover. Under emergency conditions, the slow recovery rate of the bag tended to increase the stress level or worry of the operator so that he would attempt to speed up the resuscitation cycle by either applying the next pressure stroke too soon before the bag had completely filled or, alternatively, applying it too rapidly. This would in turn, produce an excess pressure in the lungs of the user, which was precisely what the design of the bag was intended to prevent.

It has been found by experience that the great majority of operators greatly prefer a bag which has an almost immediate recovery rate. This removes a source of worry or tension, and leaves the operator free to concentrate on the condition of the patient. This in turn, leads to a more carefully controlled and relaxed application of pressure in each cycle, which leads to an improved resuscitation effect, on the patient.

It is therefore, a general objective of the invention to provide a resuscitation bag which is of integral one piece molded construction formed of thermoplastic material, and which is capable of being collapsed and stored for extended periods of time, and which when opened up for use, is provided with a significant degree of inherent resiliency, causing a rapid recovery of the shape of the bag each time it is squeezed.

BRIEF SUMMARY OF THE INVENTION

With a view to providing these advantages, and overcoming the problems of the prior art, the invention comprises a resuscitator bag of one piece integral molded construction, formed of thermoplastic material, and having a generally elongated football shape, defining an enlarged centre portion of maximum diameter, and two tapering end portions of progressively reducing diameter, and an opening at each end, inlet means at one said end, and outlet means at other said end, and each said tapering end portions having fold-rings comprising wall portions of reduced thickness, defining fold lines in said tapering end portion and ridges of greater thickness between such fold-rings whereby said end portions may be telescoped, and said enlarged centre portion having a wall thickness substantially equal to the thickness of said ridges in the tapering end portions between said rings, and there being a plurality of longitudinal ribs formed on the outer surface of said enlarged centre portion at spaced intervals around the circumference thereof, providing increased resiliency and a rapid recovery for the shape of the bag after compressing, whereby the bag may be gradually compressed, and rapidly released, without substantial delay caused by a delayed recovery of the said shape of said bag.

More particularly, the invention comprises a resuscitator bag having the foregoing advantages including further reinforcing ribs formed in said two tapering end portions, whereby to still further enhance the recovery rate of the bag.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

DESCRIPTION OF A SPECIFIC EMBODIMENT

Figure 1:
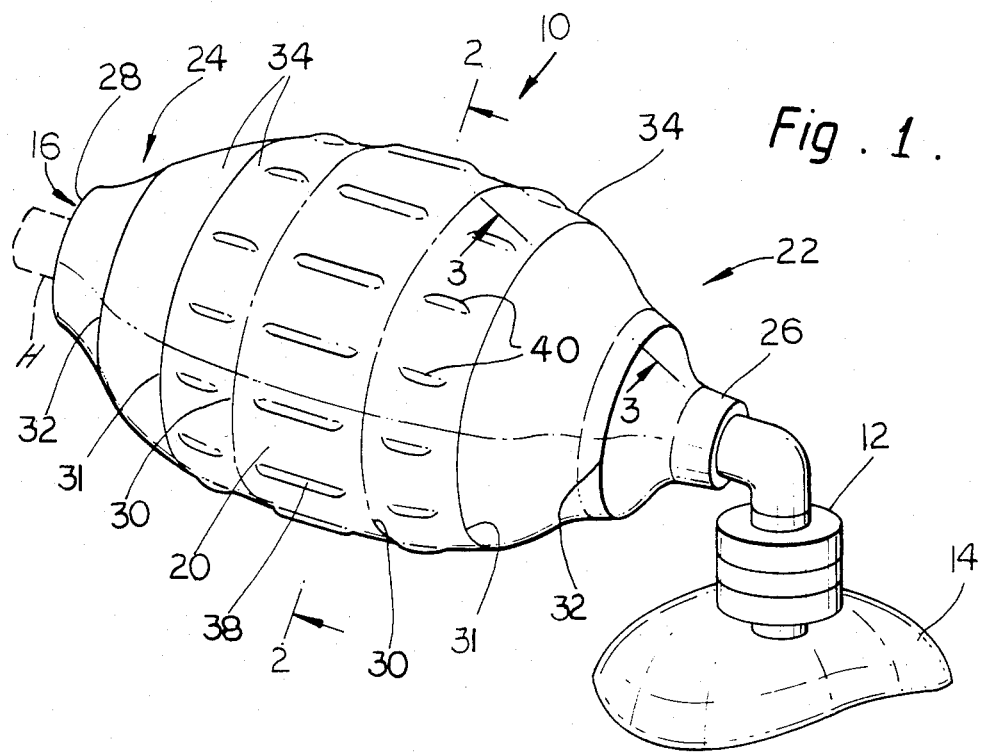
FIG. 1 is a perspective illustration showing a bag according to the invention, shown in conjunction with a typical valve and mask.
Figure 2:
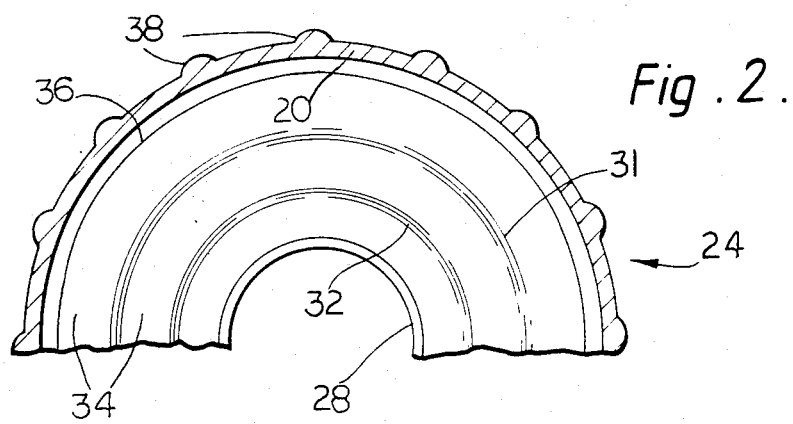
FIG. 2 is a section of the bag along the line 2—2.

As shown in FIG. 1, it will be seen that the invention comprises the resuscitator air bag 10, which is shown here used in conjunction with a breathing valve 12 and a mask 14. The bag will usually have an air intake valve indicated generally as 16. In cases where it is used in conjunction with a breathing gas supply, such a gas supply can be connected by means such as the hose H shown in phantom.

The gas supply may include a gas accumulator bag (not shown) of well-known design for collecting gas and storing it at or about atmospheric pressure.

The bag 10 is typically of such a size that it may be held in one hand, and squeezed and released, or alternatively may lie on any available surface, so that an operator may simply press down on the bag.

Usually, there is some form of swingable or rotatable connection between the bag 10 and the breathing valve 12, and if necessary, a longer piece of hose can be incorporated.

As mentioned above, this type of resuscitator equipment is designed to be used on an emergency basis in a wide variety of different locations. It is frequently required to be stored for extended periods of time, and subjected to very wide variations in ambient conditions of temperature, humidity and the like, and must nonetheless be ready for instantaneous use as soon as it is required.

Typically, it will be packed into a small container. This container may be for example a portable pouch (not shown) which may be carried on the person, or may be a small box which may be stored in any suitable emergency vehicle or at any location where an emergency is likely to arise.

For this purpose, since the bag 10 is relatively bulky, it is considered essential that the bag shall be collapsible into as small a space as possible.

It is also considered essential that the bag shall be made of a relatively inert substance such as a high quality thermoplastic material. In many cases this will be a polyvinyl plastic material, and in other cases, silicone-based materials are preferred as having an even longer storage life, and an even greater resistance to variations in ambient conditions, and therefore being less likely to deteriorate during extended periods of storage.

In order to provide these various functions, the bag is molded as an integral one-piece structure, with various integral formations providing the various different functions.

For the purpose of this explanation, the bag may be considered as having a central region 20 of maximum diameter, and two progressively tapering end portions 22–24, terminating in end collars 26–28.

The end portions 22 and 24 are intended to be infolded in a telescoping manner within the central portion 20, for packing and storage of the bag 10.

Figure 3:
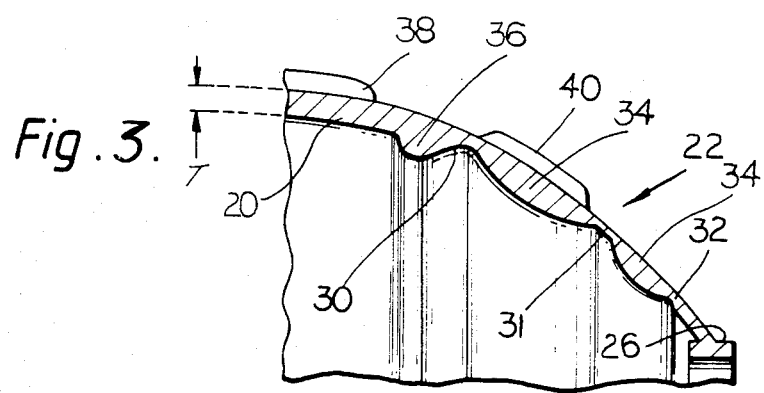
FIG. 3 is a section along the line 3—3 of FIG. 1.

In order to accommodate this function, the end portions are shown in FIG. 3 as incorporating three reduced thickness fold rings 30, 31 and 32. The ring 30 is of greater diameter and the ring 32 of lesser diameter. Thickened ridge portions 34 extend between rings. The rings permit the end portions 22 and 24 to be retracted in a generally telescoping manner. When required for use, the end portions 22–24 may be readily snapped out simply by pulling on the end connectors 26 and 28, rendering the bag 10 ready for use.

In order to provide the bag with a substantial degree of inherent resilience, the central portion 20 is made with a wall thickness shown as T, which is essentially equal to the wall thickness of the ridge portions 34 of the tapered ends 22–24. In addition, a thickened reinforcing ring 36 is provided at the transition from the central portion 20, and the first ring 30.

It is found that these characteristics provide to some degree the rapid recovery desired by operators. However, additional longitudinal reinforcing spring ribs 38 are preferably provided on the exterior of the central portion 20 aligned with the central axis of the bag 10, and arranged at spaced intervals. The spring ribs 38 extend substantially from one of the internal reinforcing rings 36 to the other, along the full longitudinal extent of the central portion 20. The spring ribs 38 function to provide an effective outward springing action to the bag, causing it to rapidly recover its original shape after it has been compressed.

In order to still further enhance this recovery rate, additional spring ribs 40 are provided on the tapering end portions 22-24. The spring ribs 40 preferably extend from the larger reduced thickness ring 30, at spaced intervals therearound to the next adjacent ring 32 of lesser diameter.

The spring ribs 38 and 40 are moulded integrally in one piece of thermoplastic material as shown, and being of the same material, consequently have the same extended storage life and resistance to deterioration.

The usage of the bag 10 is self evident from FIG. 1. In use it will normally be compressed progressively to induce inhalation. After an inhalation stroke, the bag 10 is released and allowed to recover its original shape. During this phase pressure may be applied to the chest or abdomen of the patient, causing him to exhale. In the normal case exhalation takes place through suitable ports and valving (not shown) in the breathing valve 12.

During the initial phases of resuscitation, particularly where an emergency has occurred and the patient is not breathing, four or five rapid pulses are usually administered. This is achieved by rapidly compressing and releasing the bag 10. It is found that the bag 10 as shown and described herein performs well during this rapid initial pulsing, and provides the virtually instantaneous recovery of the bag shape which is required for this type of treatment.

Where the bag is used to resuscitate an infant, the breathing rate may be much higher, i.e., sixty breaths per minute. It is not found that there is any increased danger of overpressuring the lungs, when using the bag, and in fact, the rapid recovery rate reduces operator stress and enables him to concentrate on controlling the treatment.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A manually operable resuscitator bag of one piece integral molded construction, formed of thermoplastic material, and comprising:

a generally elongated football shape, defining an enlarged center portion of maximum diameter, and two tapering end portions of progressively reducing diameter;

an opening at each end and inlet means at one said end, and outlet means at the other said end;

first fold-rings formed at about the transition from said centre portion to each of said tapering end portions, said first fold-rings comprising wall portions of reduced thickness and defining flex zones;

second fold-rings in each said tapering end portion comprising wall portions of reduced thickness, defining flex zones in said tapering end portions whereby said end portions may be telescoped, said second fold-rings being of reduced diameter relative to said first fold-rings;

ridges of thickened wall section between such fold-rings;

said centre portion having a wall thickness substantially equal to the thickness of said ridges in said tapering end portions between said rings;

a plurality of longitudinal ribs formed on the outer surface of said centre portion at spaced intervals around the circumference thereof, and terminating short of said first fold-rings, and further reinforcing ribs formed in said two tapering end portions, said further ribs extending from said first to said second fold-rings, providing increased resiliency and a rapid recovery for the shape of the bag after compressing whereby the bag may be gradually manually compressed, and rapidly released without substantial delay caused by a delayed recovery of the shape of said bag.

* * * * *

UNITED STATES PATENT AND TRADEMARK OFFICE
CERTIFICATE OF CORRECTION

PATENT NO. : 4,532,923
DATED : August 6, 1985
INVENTOR(S) : Stephen D. Flynn

It is certified that error appears in the above—identified patent and that said Letters Patent is hereby corrected as shown below:

Change the name of the Assignee to

O-TWO SYSTEMS INTERNATIONAL INC.

Signed and Sealed this

Twenty-second Day of April 1986

[SEAL]

Attest:

DONALD J. QUIGG

Attesting Officer

Commissioner of Patents and Trademarks